US011752022B2

(12) United States Patent
Fontaine

(10) Patent No.: US 11,752,022 B2
(45) Date of Patent: Sep. 12, 2023

(54) THERMOFORMABLE SEMI-RIGID ORTHOSES

(71) Applicant: MILLET INNOVATION, Loriol sur Drome (FR)

(72) Inventor: Thierry Fontaine, Marsanne (FR)

(73) Assignee: MILLET INNOVATION, Loriol sur Drome (FR)

( * ) Notice: Subject to any disclaimer, the term of this patent is extended or adjusted under 35 U.S.C. 154(b) by 507 days.

(21) Appl. No.: 15/735,212

(22) PCT Filed: Jun. 7, 2016

(86) PCT No.: PCT/FR2016/051355
§ 371 (c)(1),
(2) Date: Dec. 11, 2017

(87) PCT Pub. No.: WO2016/198778
PCT Pub. Date: Dec. 15, 2016

(65) Prior Publication Data
US 2018/0168840 A1 Jun. 21, 2018

(30) Foreign Application Priority Data
Jun. 10, 2015 (FR) .................................... 15 55282

(51) Int. Cl.
*A61F 5/01* (2006.01)
*A61D 9/00* (2006.01)
(Continued)

(52) U.S. Cl.
CPC .............. *A61F 5/0104* (2013.01); *A61D 9/00* (2013.01); *A61F 5/0106* (2013.01); *A61F 5/019* (2013.01);
(Continued)

(58) Field of Classification Search
CPC ....... B29C 44/24; B29C 51/02; B29C 51/264; B29C 51/421; A61F 5/04; A61F 5/05825;
(Continued)

(56) References Cited

U.S. PATENT DOCUMENTS

| 4,572,167 A | 2/1986 | Brunswick |
| 4,716,892 A * | 1/1988 | Brunswick ............ A61F 5/0118 |
| | | 602/21 |

(Continued)

FOREIGN PATENT DOCUMENTS

| WO | 2010/007243 A1 | 1/2010 |
| WO | 2011/111019 A1 | 9/2011 |
| WO | 2014/110029 A1 | 7/2014 |

OTHER PUBLICATIONS

Sep. 30, 2016 Search Report issued in International Patent Application PCT/FR2016/051355.

*Primary Examiner* — Ophelia A Hawthorne
(74) *Attorney, Agent, or Firm* — Oliff PLC

(57) ABSTRACT

An orthosis for supporting a limb or a joint of a human or of a vertebrate animal, including: a sleeve which is at least partly elastic and is designed to enclose a limb or a joint, a plate made of a thermoformable material, and a pocket formed on the sleeve in order to receive the plate, the pocket having a shape adapted to that of the plate. The adherence between the plate and the inner surface of the pocket is treated in order to permit a relative movement of the plate with respect to the material forming the pocket during and after an operation of thermoforming of the plate, this being done by placing the orthosis on the limb or the joint with the plate present in the pocket. This orthosis is designed to be fitted in place and thermoformed by the user himself.

16 Claims, 4 Drawing Sheets

(51) Int. Cl.
*B29C 51/02* (2006.01)
*B29C 51/26* (2006.01)
*B29C 51/42* (2006.01)
*B29L 31/00* (2006.01)

(52) U.S. Cl.
CPC .......... *A61F 5/0109* (2013.01); *A61F 5/0111* (2013.01); *A61F 5/0118* (2013.01); *B29C 51/02* (2013.01); *B29C 51/264* (2013.01); *B29C 51/421* (2013.01); *B29L 2031/753* (2013.01)

(58) Field of Classification Search
CPC ...... A61F 5/058; A61F 13/00017; A61F 5/01; A61F 5/0102; A61F 5/0109; A41D 13/05; A41D 13/01; A41D 2300/322; B29L 2031/753
USPC .............................................. 602/6–7, 63–64
See application file for complete search history.

(56) References Cited

U.S. PATENT DOCUMENTS

| | | | | |
|---|---|---|---|---|
| 5,898,938 | A * | 5/1999 | Baylor | A63B 71/143 |
| | | | | 2/161.1 |
| 6,056,713 | A * | 5/2000 | Hayashi | A61F 5/0111 |
| | | | | 602/8 |
| 6,362,387 | B1 * | 3/2002 | Carlson | A61F 5/01 |
| | | | | 602/41 |
| 9,492,304 | B2 * | 11/2016 | Fontaine | A61F 13/068 |
| 2002/0026664 | A1 * | 3/2002 | Grounds | A41D 13/012 |
| | | | | 2/467 |
| 2007/0106356 | A1 * | 5/2007 | Carstens | A41D 13/005 |
| | | | | 607/114 |
| 2013/0060181 | A1 | 3/2013 | Fontaine et al. | |
| 2015/0335460 | A1 | 11/2015 | Weaver, II et al. | |
| 2016/0095737 | A1 * | 4/2016 | Rich | A43B 7/141 |
| | | | | 602/7 |

* cited by examiner

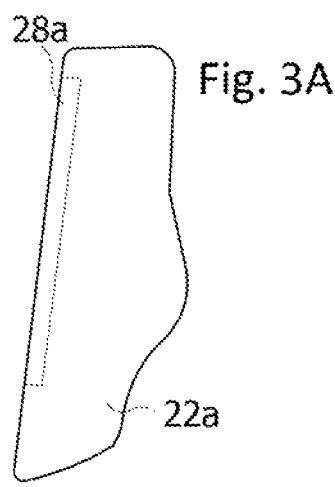
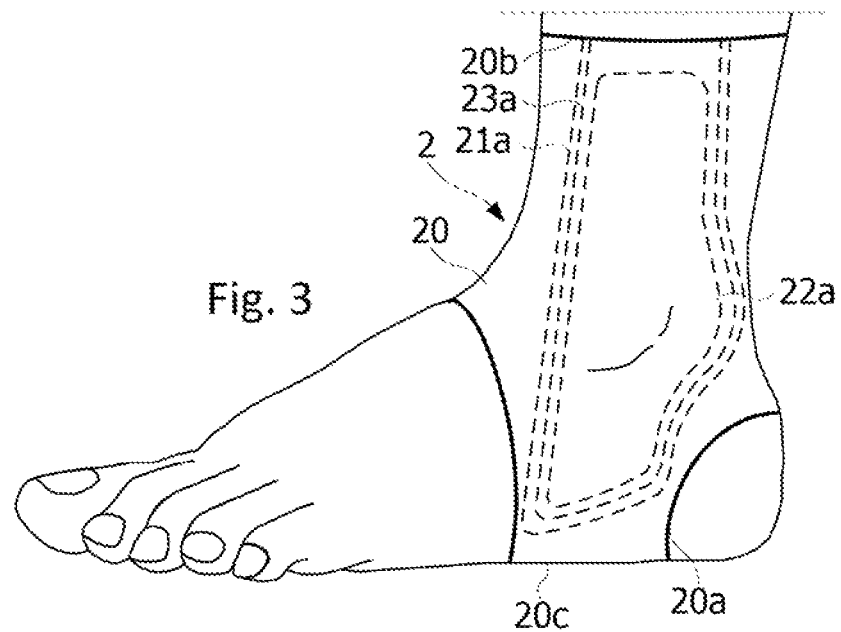
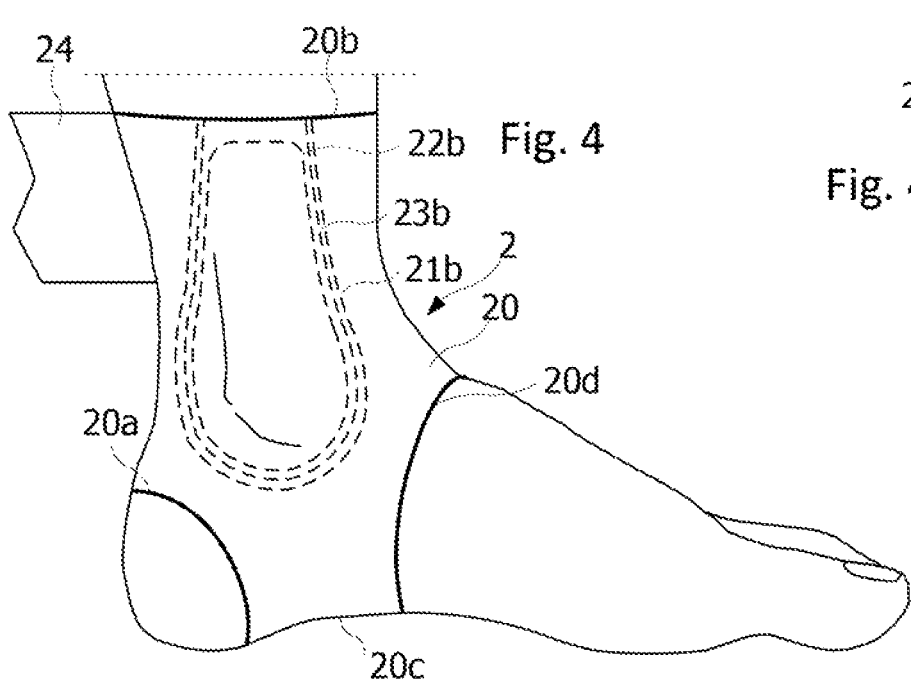
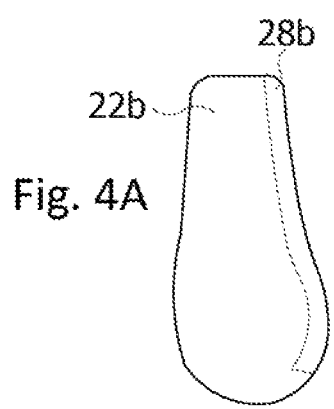

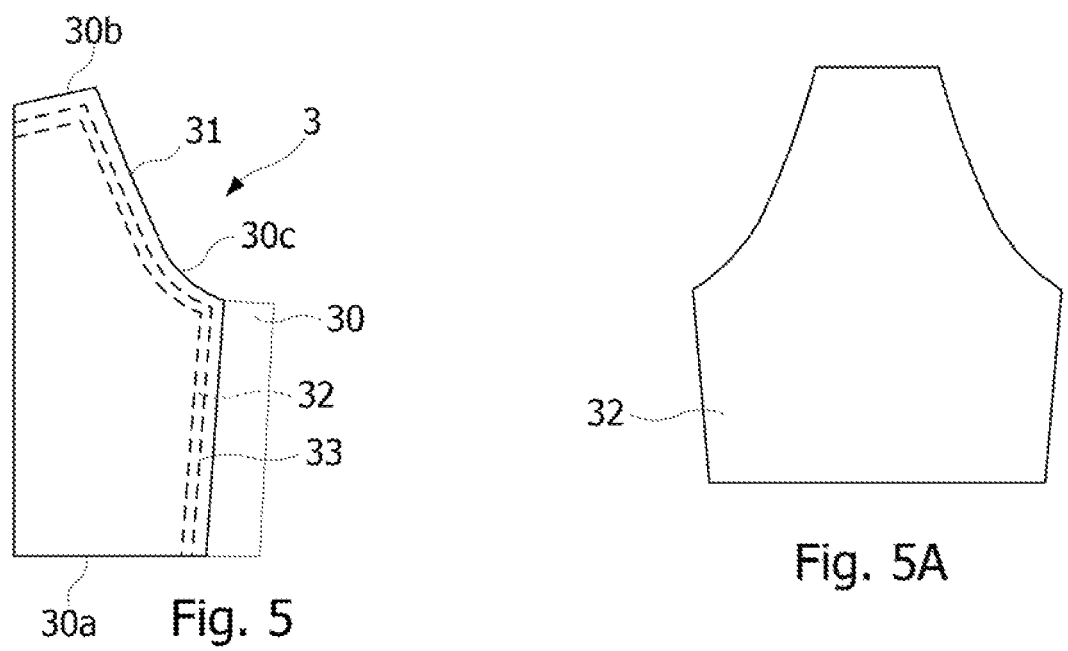
Fig. 5
Fig. 5A
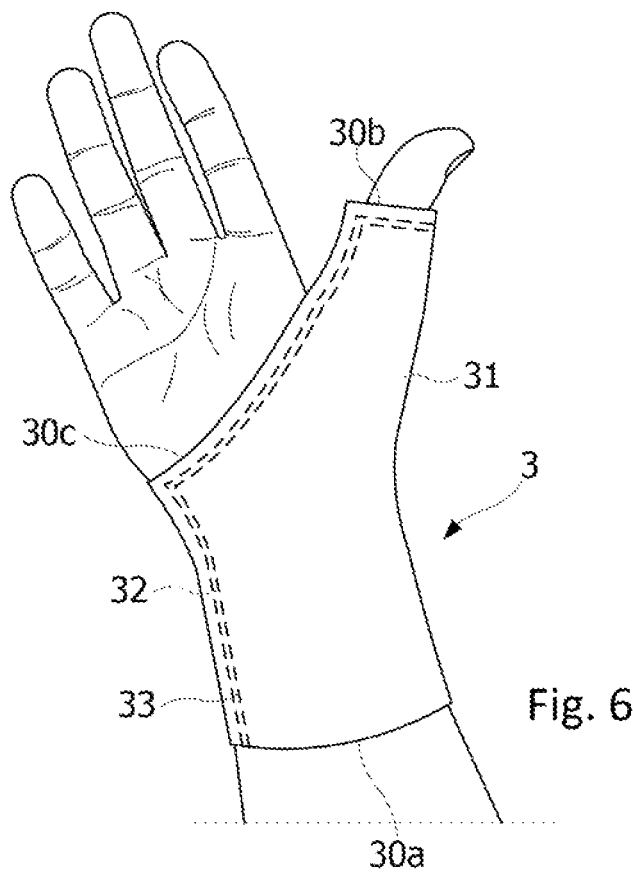
Fig. 6

THERMOFORMABLE SEMI-RIGID ORTHOSES

FIELD

The present invention relates to orthoses intended to limit the movements of a limb or corrective orthoses such as those used, for example, for the treatment of Hallux Valgus by realigning the articulation of the big toe under mechanical effect.

BACKGROUND

In the design of lightweight orthoses, two categories of situations can be identified, for which it is required to provide rigid elements adapted to the shape of the limb to maintain. In some situations, it is required to immobilize a limb. This is the case with the thumb when it comes to relieving the effects of rhizarthrosis. This is also the case when a limb must be held in a certain position, especially for a treatment requiring a high degree of precision, for example to position a person under a radiotherapy apparatus for the treatment of cancer.

To treat certain joint trauma including the ankle or wrist, it may also be required to ensure some maintenance of the joint. In other situations, it may also be required to tension a joint for a corrective purpose. This is the case, for example, of the big toe to treat a hallux valgus. In the case of certain joints such as the ankle, it may be useful to prevent trauma by maintaining the joint during the practice of certain exercises such as walking. Retention can compensate for the laxity of a joint.

To meet requirements of rigidity and adaptation to the shape of the limb and/or of the joint to maintain, orthotists use hot thermoformable materials, whose shape can be modified at will by further hot forming. A plate of such material is generally heated by immersing it for a few minutes in hot water at a temperature that is tolerable to the patient. The plate then becomes soft enough to conform to the shape of the area to be maintained, before it hardens.

Currently, orthotists make custom orthoses including a thermoformable material, following procedures defined by the manufacturers of these materials. It turns out that all these procedures cannot be performed by the patient himself, and are usually intended to be implemented by professionals. In addition, orthoses made in accordance with these procedures are relatively heavy and bulky, due in particular to the use of heavy and thick knitwear and fastening bands with loops and hooks (Velcro-type).

From documents WO 2014/110029, U.S. Pat. No. 4,716,892 and U.S. Pat. No. 4,572,167, it is known to use this type of material by placing it in a generally open pocket, associated with an open enveloping system that the practitioner closes while applying it firmly on the limb to obtain its shape.

It is therefore desirable to provide an orthosis adapted to ensure a rigid retention of a limb or a joint. It may also be desirable for this orthosis to be lighter and less cumbersome than the orthoses currently used. It may also be desirable that this orthosis be adaptable and/or usable without requiring the aid of a professional.

SUMMARY

Embodiments relate to an orthosis for maintaining a limb or joint of a human or vertebrate animal, comprising: an at least partially elastic sleeve, and shaped to compress a limb or joint, a plate made of a thermoformable material, and a pocket formed on the sleeve for receiving the plate, the pocket having a shape adjusted to that of the plate.

According to an embodiment, the pocket is formed by a layer attached on an inner face of the sleeve, configured to contact the skin of the limb or the joint to be maintained.

According to an embodiment, the pocket is formed by a layer attached to the sleeve, made of a padded fabric.

According to an embodiment, the portion of the sleeve not covered by the pocket is made of an elastic fabric.

T According to an embodiment, wherein the sleeve is made of an elastic fabric having a thickness between 0.2 and 1.5 mm.

According to an embodiment, the plate and/or the inner faces of the pocket configured to contact the plate are covered with a film or a coating to reduce the adhesion between the plate and the inner faces of the pocket during and following a thermoforming operation of the plate while the plate is placed in the pocket.

According to an embodiment, the plate is cut from anti-adhesion-treated sheet material, and a portion of the plate edges is covered with a strip that does not adhere to the inner faces of the pocket and limits the adhesion between the plate and the inner faces of the pocket during and after a thermoforming operation of the plate.

According to an embodiment, the sleeve is adapted to one of the following shapes: the shape of the ankle and foot of a human, with a proximal opening for the passage of the leg, a distal opening for the passage of the forefoot, and an intermediate opening for the passage of the heel, the sleeve including two pockets for covering the malleoli of the ankle extending between the base of the foot and the proximal opening of the sleeve, the two pockets being configured to receive two plates of a thermoformable material; the shape of the wrist and a proximal part of the hand and thumb of a human, with a distal opening for the passage of the distal portion of the thumb, a proximal opening for the passage of the forearm, and an intermediate opening for the passage of the fingers of the hand, the sleeve including a pocket for covering the entire sleeve except for a portion of the sleeve that covers the side of the hand, the pocket being configured to receive the plate of a thermoformable material; the shape of the foot and a proximal portion of the big toe of a human, with a distal opening for the passage of the distal portion of the big toe, a proximal opening for the passage of the foot, and an intermediate opening for the passage of the other toes of the foot, the sleeve including a pocket on a portion of the sleeve configured to cover a portion of the internal lateral face of the foot and big toe, the pocket being configured to receive the plate of a thermoformable material.

According to an embodiment, the sleeve is adapted to the shape of the ankle and the foot of a human, the sleeve being secured to a band configured to be wrapped around the foot and the ankle, to further tighten the sleeve around the foot and the ankle, especially during the thermoforming of the plate.

According to an embodiment, an outer face of the pocket, configured to contact the skin of the limb or the joint to be maintained, is coated with a polymer gel layer, the portion of the pocket coated with polymer gel having an elasticity in the direction perpendicular to the axis of the limb, greater than or equal to that in a direction parallel to the axis of the limb.

According to an embodiment, the orthosis comprises a polymer gel pellet removably attached to the outer surface of the pocket coated with a polymer gel.

Embodiments may also relate to a method of manufacturing an orthosis for maintaining a limb or joint of a human or vertebrate animal, comprising steps of: fabricating an at least partially elastic sleeve, shaped to compress a limb or joint, adjusting the shape of a plate of a thermoformable material to a portion of the limb or joint, and forming a pocket on the sleeve for receiving the plate, the pocket having a shape adjusted to that of the plate.

According to an embodiment, the formation of the pocket is performed by attaching a layer on an inner face of the sleeve, configured to contact the skin of the limb or the joint to be maintained.

Embodiments may also relate to a of manufacturing an orthosis for maintaining a limb or joint of a human or a vertebrate animal, comprising steps of implementing the previously defined manufacturing method and placing the plate in the pocket, as well as a thermoforming operation of the orthosis comprising the steps of: heating the orthosis to a temperature sufficient to soften the plate, and placing the sleeve around the limb or joint before the plate hardens.

According to an embodiment, the thermoforming operation comprises a step of covering the limb or joint with a film prior to placing the sleeve around the limb or joint.

According to an embodiment, the thermoforming operation comprises a step of placing a pellet on an area of the outer face of the pocket configured to contact the skin, before placing the sleeve around the limb or the joint, the pellet being removed from the sleeve after the thermoforming operation, so as to form a gap between the plate and the skin.

BRIEF DESCRIPTION OF DRAWINGS

Exemplary embodiments of the invention will be described in the following, without limitation in connection with the accompanying drawings:

FIG. 3A shows a thermoformable part of the ankle orthosis of FIG. 3, according to an embodiment, FIG. 4 schematically shows the internal lateral face of the foot and the ankle, fitted with the orthosis shown in FIG. 3, FIG. 4A represents another thermoformable part of the ankle orthosis of FIG. 3, according to an embodiment, FIG. 5 schematically shows a thumb orthosis according to an embodiment, FIG. 5A shows a thermoformable part of the thumb orthosis of FIG. 5, according to an embodiment, FIG. 6 shows a hand and a wrist fitted with the thumb orthosis of FIG. 5, FIG. 7 schematically shows a corrective orthosis for hallux valgus according to an embodiment.

DESCRIPTION OF EMBODIMENTS

Figure 1:
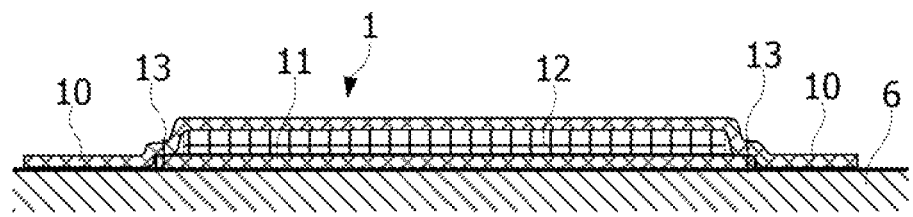
FIG. 1 is a schematic sectional view of an orthosis according to one embodiment, FIGS. 2A to 2F schematically show, in section view, a pan of the orthosis at different times of a thermoforming operation, FIG. 3 schematically shows the external lateral face of a foot and ankle, fitted with an ankle orthosis according to an embodiment.

FIG. 1 shows an orthosis 1 according to an embodiment. The orthosis 1 includes two layers 10, 11. The layer 10 is at least partly elastic, and shaped to form a sleeve adjusted around a limb or a joint to maintain by exerting a certain pressure. The layer 11 is attached over the layer 10 so as to form a pocket in which a plate 12 of a thermoformable material is inserted. The shape of the pocket is adjusted to that of the plate 12. Thus, the degree of filling of the pocket by the plate may be between 80 and 95%. The shape of the plate 12 may itself be defined according to a region of the limb or articulation where the maintenance is to be ensured.

The layer 10 may be brought into direct contact with the skin 6 of the patient. The layer 11 may be attached on the layer 10 by a weld or seam line 13, on one or the other of the faces of the layer 10.

Figure 2A:
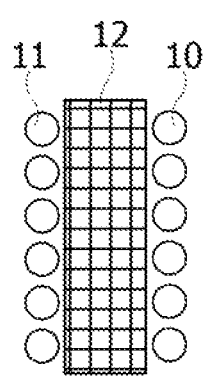
Figure 2B:
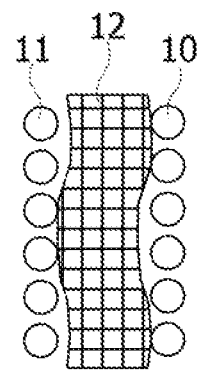
Figure 2C:
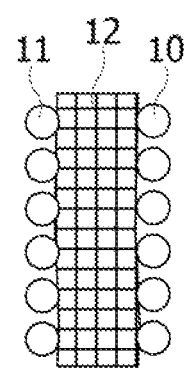
Figure 2D:
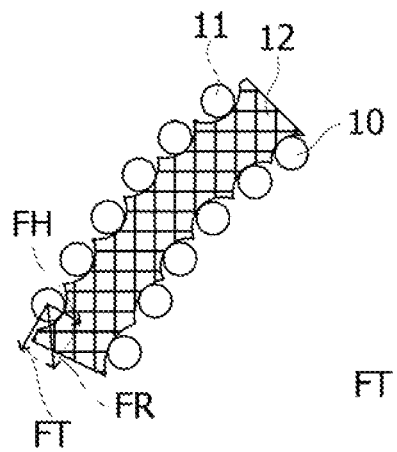
Figure 2E:
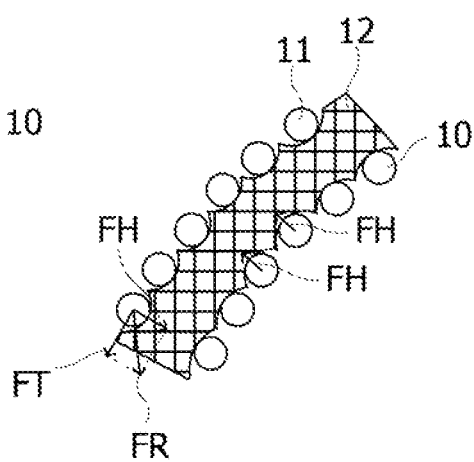
Figure 2F:
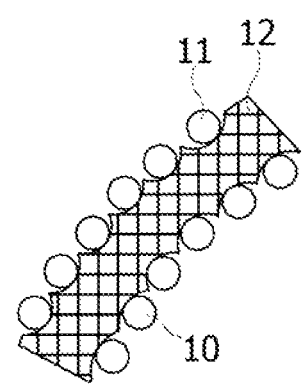

The orthosis 1 can be used in the following manner, illustrated by FIGS. 2A to 2F. FIGS. 2A to 2F show a portion of the plate 12 and threads forming the layers 10, 11. Before a first use, the orthosis (FIG. 2A) should undergo a thermoforming operation. For this purpose, it is heated, for example by immersing it in hot water, with the plate 12 placed in the pocket, at a temperature sufficient to soften the plate 12. From a certain time after its contact with the hot water, the plate 12 becomes soft (FIG. 2B). The orthosis is then removed from the hot water and wiped, which makes the threads of the layers 10, 11 penetrate slightly in the plate 12 due to the ductility of the plate in its soft state (FIG. 2C). Before the plate regains its rigidity, the patient fits the orthosis around the member or joint to maintain by expanding the sleeve formed by the layer 10 (FIG. 2D), preferably by pulling on the areas outside the pocket and plate. Due to its ductility, the plate 12 is then slightly stretched. The prints formed by the threads of the fabric in the plate 12 may then slightly widen. The sleeve is then released (FIG. 2E). The elastic tension exerted by the layer 10 around the limb or articulation applies the plate 12 against the skin of the patient. Due to its malleability, the plate 12 then takes the shape of the area where it is applied, then hardens after a few minutes. During hardening of the plate (FIG. 2F), the limb to be maintained is held in the desired final position. The orthosis thus adapts to the morphology of the zone where it is applied, through thermoforming of the plate 12, achieved simply by fitting the orthosis over the limb, causing elastic forces exerted by the layer 10 ensuring the maintenance, and the deformation of the pre-softened plate 12. This operation does not require the intervention of another person and in particular a professional. This result is achieved by combining the properties of the fabric and the tension of the fabric around the limb, as well as the properties of the interface between the fabric and the plate 12, and in particular the coefficient of friction between the plate and the fabric, and the ductility of the plate.

Before the thermoforming operation, the portion of the limb or joint to be maintained may be covered with a film such as a plastic film to facilitate removal of the wet orthosis at the end of the thermoforming operation.

The plate 12 is for example made of a material such as "Aquaplast" manufactured by Patterson, and has a thickness of between 1.5 and 5 mm, for example about 1.6 mm. This material becomes soft at 65-75° C. and remains malleable for about four minutes. Thus, the thermoforming operation of the plate 12 can be repeated as many times as necessary.

The layer 11 located between the skin of the patient and the plate 12 may be made of a sufficiently thick padded fabric (between 1 and 2 mm thick) to limit the discomfort that may result from the application of a rigid plate on the skin. The layer 10 may be made of an elastic fabric having a thickness between 0.2 and 1.5 mm, for example about 0.5 mm. These arrangements enable production of lightweight and space-saving orthoses while offering the same services as existing orthoses that are heavier and cumbersome, and without requiring the intervention of a professional.

It may be desirable to enable removal of the plate from its pocket after thermoforming. It may also be desirable to avoid strong adhesion between the plate 12 and the areas of the layers 10, 11 in contact with the plate. Indeed, such adhesion would make the fabric in these areas inelastic and prevent a uniform distribution of the tension exerted by the sleeve formed by the layer 10 around the limb or joint. Such adhesion may also prevent subsequent accurate positioning of the plate 12 on the limb or joint.

It turns out that the threads of the fabric forming the layers 10 and 11 can embed in the material of the plate 12 because of the ductility of the plate, to the extent that it can be very difficult to separate the plate 12 from the layers 10, 11 at the end of the thermoforming operation. This embedding effect occurs in particular when the sleeve formed by the layer 10 is expanded while fitting the orthosis around the limb or joint, and while the plate hardens during the thermoforming operation.

However, thermoformable materials are generally very ductile and this property is sought to fit a shape as accurately as possible. Therefore, the use of a low ductility interface between the plate 12 and the fabric 10, 11 would necessarily affect the accuracy of the thermoforming process, particularly in areas of the limb or joint with large variations in radius of curvature. Moreover, for reasons of comfort and health, it is difficult to compensate for this effect by increasing the elastic tension exerted by the layer 10 on the region of the body covered by the orthosis. In addition, there are standards imposing maximum values of compression.

The plate 12 can be covered with a film or a coating before inserting it into the pocket formed in the orthosis. A surface treatment such as coating may also be applied to the layers 10, 11 inside the pocket to reduce the ridges formed on the plate by the threads of the fabric forming these layers, and thus reduce the adhesion of the thermoformable material that can be noted after the thermoforming operation. Stretching and then releasing the sleeve during thermoforming, when the plate material is soft, also tends to widen the prints formed by the fabric threads in the plate 12.

According to an embodiment, the plate 12 is cut from sheet material that has been surface-treated to reduce its adhesion to the fabric of the layers 10, 11. The plate can thus for example be coated with a thin layer of PTFE (Poly Tetra Fluoro Ethylene). It follows, for reasons previously explained, that the edges of the plate 12 may strongly adhere to the fabric by embedding the threads of the fabric in the thermoformable material forming the plate 12, since the core of the thermoformable material cannot receive an anti-adhering treatment. If the entire periphery of the plate 12 strongly adheres to the fabric, the elasticity of the fabric in contact with the plate 12 cannot be used, which also prevents a uniform distribution of the elastic tension exerted by the layer 10 on the area of the body covered by the orthosis.

According to an embodiment, a portion of the edges of the plate 12 is covered by a strip that does not adhere to the fabric, formed in a material preventing the threads of the fabric 10, 11 forming the pocket from embedding in the material of the plate or limiting embedding during the thermoforming operation. This material may, for example, be based on nonwoven fibers. The portion of the edges of the plate 12 covered with the strip may be limited to one side of the plate in contact with an area of the layers 10, 11 intended to be stretched perpendicularly to the considered side of the plate.

Thus, when the sleeve is stretched to fit the orthosis (FIG. 2D), the threads of the layers 10, 11 form prints in the plate 12. These prints are wider than the diameter of the threads, since the latter exert forces FH, FT both perpendicular to the surface of the plate 12 and tangential to this surface. Thus, the prints do not prevent movements of the plate 12 relative to the fabric (10, 11) forming the pocket. During the actual thermoforming operation, the sleeve is released (FIG. 2E). Because the prints are wider than the diameter of the threads, the fabric (10, 11) forming the pocket can adjust on the plate 12 as the sleeve is released. Thus, in regions with a small radius of curvature, the threads of the fabric 10, 11 forming the pocket exert a substantially perpendicular force FH on the surface of the plate 12. As one moves away from such a region, the force exerted by the threads has an increasing component FT tangential to the surface of the plate. The force FR resulting from the forces FH and FT presses the plate 12 against the limb independently of the curvatures of the region of the limb covered by the plate 12.

If the interface between the plate 12 and the fabric was not treated for preventing adhesion, the threads of the fabric (10, 11) would embed into the plate 12 and therefore their respective positions would be frozen during the stretching and loosening of the sleeve. The elasticity of the fabric in the regions of contact with the plate 12 would then be that of the plate, which is very rigid in the hardened state.

With these provisions, an accurate thermoforming of the plate 12 can be obtained by conforming the sleeve corresponding to the layer 10 so that it exerts a pressure on the limb or articulation between 2.5 and 5 hPa. These values were measured on an ankle orthosis as shown in FIGS. 3 and 4.

FIGS. 3 and 4 show an orthosis 2 adapted to maintain the ankle, for example following a trauma. Orthosis 2 has the structure of orthosis 1 (FIG. 1). Thus, the orthosis 2 comprises a layer 20 forming a sleeve shaped to compress the ankle and the foot, with a proximal opening 20b for the passage of the leg, a distal opening 20d for the passage of the foot and an intermediate opening 20a for the passage of the heel. The layer 20 is at least partly elastic. A layer 21a is fixed on the layer 20 so as to form a first pocket in which is inserted a first plate 22a of a thermoformable material. The shape of the first pocket is adjusted to that of the plate 22a. The first pocket is formed on the layer 20 at a location corresponding to the external malleolus and extends laterally between the openings 20a and 20d and between the proximal opening 20b of the layer 20 and a portion 20c of the layer 20 covering a lateral side of the foot between the plantar and dorsal areas. The shape of the plate 22a is shown in FIG. 3A. The first pocket is formed by attaching the layer 21a on the layer 20 along a fastening line 23a. The first pocket has for example an opening along the proximal opening 20b of the sleeve 20, for inserting or removing the plate 22a from the pocket.

According to an embodiment, the orthosis 2 comprises a second plate 22b made of a thermoformable material placed in a second pocket formed on the layer 20 at a location intended to cover the internal malleolus and extending laterally over the layer 20 around the internal malleolus to the opening 20b of the sleeve 20. The shape of the plate 22b is shown in FIG. 4A. The second pocket is formed using a layer of fabric 21b attached on the sleeve 20 along a fastening line 23b. The second pocket may also have an opening along the proximal opening 20b of the sleeve 20 to insert or remove the plate 22b from the pocket.

If necessary, a band 24 (part of which is shown in FIG. 4) intended to be wound and tightened around the foot and ankle, can be used to further tighten the orthosis around the ankle and foot.

As explained above, a portion of the edges of plates 22a, 22b may be covered with a strip 28a, 28b that does not adhere to the fabrics forming the layers 20, 21a, 21b and prevents embedding of the threads of these fabrics in the edges of the plates 22a, 22b. In the example of FIGS. 3A, 4A, the strips 28a, 28b cover most of the anterior edges (towards the front of the foot) of the plates 22a, 22b.

FIGS. 5 and 6 show an orthosis 3 designed to maintain the thumb, in particular to relieve patients suffering from rhizarthrosis, ensuring thumb retention especially during the night. The orthosis 3 has the structure of the orthosis 1 (FIG. 1). Thus, the orthosis 3 includes two layers 30, 31. The layer 30 is at least partly elastic. The layer 31 is attached on the layer 30 so as to form a pocket in which is inserted a plate 32 of a thermoformable material. The shape of the pocket is adjusted to that of the plate 32. The orthosis 3 is shaped to maintain the rectitude of the thumb and the first metacarpal, according to an embodiment. For this purpose, it has the shape of a sleeve configured to compress the base of the hand with the wrist and the two phalanges of the thumb, having a proximal opening 30a for the passage of the forearm, a distal opening 30b for the passage of the distal end of the thumb, and an intermediate opening 30c for the passage of the other fingers of the hand. The plate 32, as shown in particular in FIG. 5A, is shaped to cover the first phalanx of the thumb and the articulation between this first phalanx and the first metacarpal, the base of the hand and the wrist, with the exception of the region of the ulnar edge of the hand. The pocket is formed on the layer 30 at a location corresponding to the parts to be covered by the plate 32. Thus, the pocket extends over the entire sleeve with the exception of a portion of the sleeve that covers the region of the ulnar edge of the hand. The pocket is formed by attaching the layer 31 on the layer 30 along a fastening line 33. The pocket has, for example, an opening along the proximal opening 30a of the sleeve 30 to insert or remove the plate 32 from the pocket. The portion of the layer 30 not covered by the layer 31 is sufficiently elastic to allow removal of the orthosis, especially when the plate 32 has been thermoformed. The elastic tension of the layer 30 is sufficient to press the plate 32 against the skin during its thermoforming while in position on the hand. A band may be associated with the sleeve to strengthen compression, if necessary, during thermoforming. According to an embodiment, this band is removed after thermoforming.

Instead of a single pocket and a single plate, a palmar pocket and a back pocket may be provided, designed to receive two plates of a thermoformable material.

Figure 7:
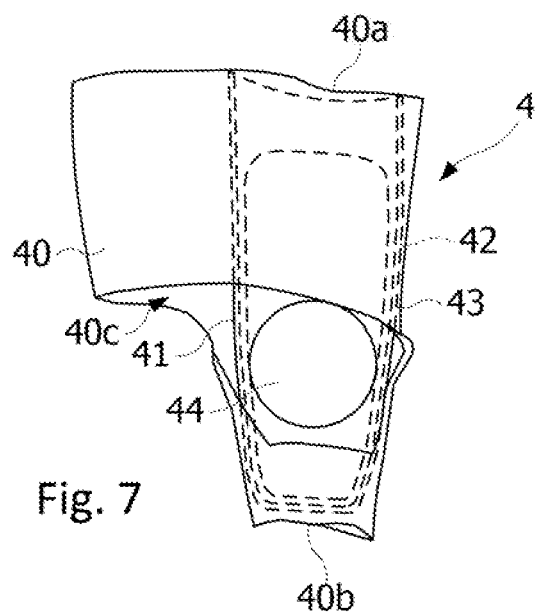
FIG. 7A shows a thermoformable part of the corrective orthosis of FIG. 7, according to an embodiment.
Figure 7A:
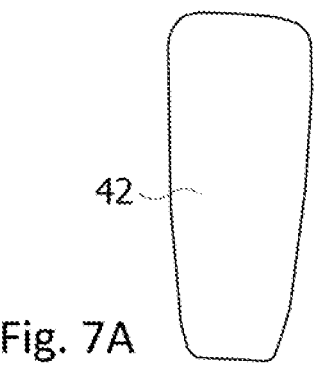
Figure 8:
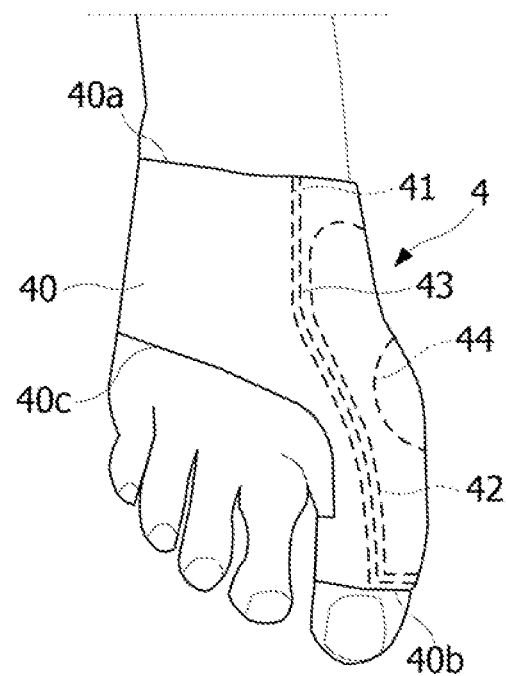
FIG. 8 shows a foot fitted with the corrective orthosis of FIG. 7.

FIGS. 7 and 8 show an orthosis 4 designed for treating a hallux valgus, especially during the night, exerting forces tending to realign the proximal phalanx of the big toe with the first metatarsal. For this purpose, the orthosis 4 is shaped to maintain the big toe in the extension of the first metatarsal, according to an embodiment. The orthosis 4 has the structure of the orthosis 1 (FIG. 1). Thus, the orthosis 4 comprises two layers 40, 41. The layer 40 is at least partly elastic. The layer 41 is attached on the layer 40 to form a pocket in which is inserted a plate 42 of a thermoformable material. The shape of the pocket is adjusted to that of the plate 42. The layer 40 has the shape of a sleeve configured to compress the foot, with a portion surrounding the big toe, a proximal opening 40a for the passage of the foot, a distal opening 40b for the passage of the distal end of the big toe, and an intermediate opening 40c for the passage of the other toes of the foot. The plate 42 as shown in particular in FIG. 7A, is shaped to cover the inner edge of the foot along the first metatarsal, and the articulation between the big toe and the first metatarsal, to the articulation between the phalanges of the big toe. The pocket is formed on the layer 40 at a location corresponding to the parts to be covered by the plate 42. The pocket is formed by attaching the layer 41 on the layer 40 along a fastening line 43. The pocket has, for example, an opening along the proximal opening 40a of the sleeve 40, for inserting or removing the plate 42 from the pocket. The portion of the sleeve 40 not covered by the layer 41 is sufficiently elastic to allow removal of the orthosis, especially when the plate 42 has been thermoformed. The tension of the layer 40 around the foot is sufficient to apply the plate 42 against the skin during the thermoforming operation of the orthosis in place on the foot. During the thermoforming of the plate 42, the big toe is maintained as much as possible in the axis of the first metatarsal. Once thermoformed, the plate 42 acts as a lever between the first metatarsal and the big toe to exert a realignment action of the first metatarsal and the proximal phalanx of the big toe. To fully play its role of a high rigidity lever, the plate may have a thickness between 2 and 5 mm, for example about 3.2 mm. However, it can be observed in FIG. 8 that the plate 42, once thermoformed, has a curved section in a plane perpendicular to the axis of the foot, that is to say in the direction where it is desirable that the plate has a high rigidity. This curved section contributes to the rigidity of the plate 42 along this axis.

According to an embodiment, the layer 41 forming the pocket with the layer 40 is made of an elastic fabric coated on one side with a layer of a polymer gel such as a silicone gel (or PDMS-polydimethylsiloxane), presenting a thickness between 0.4 and 0.6 mm. The polymer gel coated face of the fabric is designed to contact the skin. Since the used polymer gel has a coefficient of friction with the skin that is higher than that of the fabric of the layer 41, this polymer gel layer prevents the orthosis from sliding on the skin towards the front or towards the rear of the foot, or around the big toe, and therefore avoids bad positioning of the plate 42. It is preferable that the polymer gel-coated fabric has an elasticity in the direction perpendicular to the axis of the foot greater than or equal to the elasticity of the fabric in the direction parallel to the axis of the foot.

According to an embodiment, a flexible pellet 44 is placed before thermoforming, on the layer 41 (inside the orthosis), on an area intended to cover the articulation between the first metatarsal and the big toe. The pellet 44 is removed after thermoforming to leave a gap that prevents the orthosis from exerting pressure on the joint between the big toe and the first metatarsal. A further thermoforming operation of the plate 42 in the presence of the pellet 44 can be performed if necessary, to adjust the realignment forces exerted by the orthosis, and continue the corrective action of the orthosis.

The pellet 44 may have a lenticular shape and be made of a smooth polymeric gel, such as a smooth silicone gel. Thus, thanks to the properties of the silicone gel, the pellet 44 naturally adheres to the polymer gel layer, also smooth, coating the layer 41. This adhesion effect guarantees that the pellet 44 remains in place, in particular when the orthosis is immersed in hot water to carry out the thermoforming operation. This adhesion effect may be reinforced by configuring the pellet 44 with a concave face causing a suction effect. Such a concave face may be easily obtained if the pellet is formed from a liquid poured into a mold and then polymerized. Indeed, the surface tension of the liquid makes the surface of the liquid rise along the edge of the mold.

The orthoses 2 to 4 which have been described herein are adjusted to the area of the limb or joint to maintain. The shape of the thermoformable plate is also adjusted to the area to be maintained. Furthermore, the plate is arranged in a fixed pocket relative to the orthosis and whose dimensions correspond to those of the plate, whereby the plate cannot move in the pocket. These provisions ensure that the plate is positioned correctly relative to the limb or the joint to maintain. As a result, the adaptation of the orthosis to a patient does not require the intervention of a professional. In addition, the thermoforming of the plate can be performed simply by fitting the orthosis with the heated plate directly on the limb or joint to be maintained, the position of the orthosis on the limb or the joint to be maintained being defined by the shape of the orthosis. As a result, the thermoforming operation can be performed directly by the patient himself without the help of another person. To take into account variations in morphology from one person to another, it can be envisaged to manufacture each type of orthosis in several sizes, for example three or four different sizes.

It will be apparent to those skilled in the art that the present invention is susceptible to various alternatives and applications. In particular, the invention is not limited to the applications described, but can be applied to any other limb or joint, including a limb or joint of a vertebrate animal.

Furthermore, other materials than fabrics may be used to make the sleeve and the pocket, such as films or microporous membranes assembled by welding.

The invention claimed is:

1. An orthosis for maintaining a limb or joint of a human or a vertebrate animal, the orthosis comprising:
   a sleeve formed of a single piece of elastic fabric shaped to compress the limb or the joint,
   a plate made of a thermoformable material which is in a malleable state at a temperature between 65 and 75° C. and in a rigid state at a room temperature, and
   a pocket formed on the sleeve and configured to receive the plate, the pocket having a shape corresponding to a shape of the plate,
   wherein
      a surface of the plate is covered with a coating, the coating being configured to prevent threads of the elastic fabric from being embedded in the plate, the embedding resulting from a thermoforming operation of the plate, the thermoforming operation including placing the orthosis on the limb or the joint with the plate in the malleable state in the pocket, the prevention of embedding enabling relative movement of the plate with respect to the elastic fabric forming the pocket when the plate is in the pocket during and after the thermoforming operation, and
      the sleeve is configured to provide a suitable tension around the limb or the joint, during the thermoforming operation which shapes the plate in the pocket to a morphology of a region of the limb or joint where the plate is applied, and when the sleeve is worn at the room temperature with the plate in the rigid state in the pocket.

2. The orthosis according to claim 1, wherein the sleeve is adapted to one of the following shapes:
   a first shape of a distal part of a leg including an ankle and a foot of a human, the first shape including:
      a proximal opening configured to receive the leg,
      a distal opening configured to receive a forefoot of the foot, and
      an intermediate opening configured to receive a heel of the foot, the sleeve including two pockets for covering a malleoli of the ankle and extending between a base of the sleeve and the proximal opening of the sleeve, the two pockets being configured to respectively receive two plates of the thermoformable material;
   a second shape of a forearm including a wrist and a proximal part of a hand and a thumb of the human, the second shape including:
      a distal opening configured to receive a distal portion of the thumb,
      a proximal opening configured to receive the forearm, and
      an intermediate opening configured to receive fingers of the hand, the sleeve including a pocket for covering the sleeve except for a portion of the sleeve covering a side of the hand, the pocket being configured to receive the plate;
   a third shape of a foot of the human and a proximal portion of a big toe of the foot, the third shape including:
      a distal opening configured to receive a distal portion of the big toe,
      a proximal opening configured to receive the foot, and
      an intermediate opening configured to receive remaining toes of the foot, the sleeve including a pocket on a portion of the sleeve configured to cover a portion of an internal lateral face of the foot and the big toe, the pocket being configured to receive the plate.

3. The orthosis according to claim 2, wherein an outer face of the pocket is configured to contact skin of the limb or the joint to be maintained, the outer face of the pocket is coated with a polymer gel layer, a portion of the pocket coated with polymer gel having an elasticity in a direction perpendicular to an axis of the limb greater than or equal to an elasticity in a direction parallel to the axis of the limb.

4. The orthosis according to claim 3, further comprising a polymer gel pellet removably attached to the outer surface of the pocket and coated with a polymer gel layer.

5. The orthosis according to claim 2, wherein the sleeve is adapted to the first shape, the sleeve being secured to a band configured to be wrapped around the foot and the ankle so as to tighten the sleeve around the foot and the ankle during the thermoforming operation of the plate.

6. The orthosis according to claim 1, wherein the pocket is formed by a layer attached on an inner face of the sleeve, the layer being configured to contact skin of the limb or the joint to be maintained.

7. The orthosis according to claim 1, wherein the pocket is formed by a layer attached to the sleeve, the layer being made of a padded fabric.

8. The orthosis according to claim 1, wherein the elastic fabric of the sleeve has a thickness between 0.2 and 1.5 mm.

9. The orthosis according to claim 1, wherein the coating is configured to reduce adhesion between the plate and inner faces of the pocket during and after the thermoforming operation of the plate.

10. The orthosis according to claim 1, wherein the plate is cut from an anti-adhesion-treated sheet material, and an edge portion of the plate is covered with a strip configured to refrain from adhering to inner faces of the pocket and limiting adhesion between the plate and the inner faces of the pocket during and after the thermoforming operation.

11. A method of manufacturing an orthosis for maintaining a limb or a joint of a human or vertebrate animal, the method comprising:

fabricating a sleeve formed of a single piece of elastic fabric, the sleeve configured to compress the limb or the joint, adjusting a shape of a plate made of a thermoformable material to a portion of the limb or the joint, the thermoformable material being in a malleable state at a temperature between 65 and 75° C. and in a rigid state at a room temperature, forming a pocket on the sleeve for receiving the plate, the pocket having a shape adjusted to that of the plate, and covering a surface of the plate with a coating, the coating being configured to prevent threads of the elastic fabric from being embedded in the plate, resulting from a thermoforming operation of the plate, the thermoforming operation including placing the orthosis on the limb or the joint with the plate in the malleable state in the pocket, the prevention of embedding enabling relative movement of the plate with respect to the elastic fabric forming the pocket during and after the thermoforming operation; wherein the single piece of elastic fabric forming alone the sleeve is configured to provide a suitable tension around the limb or the joint, during the thermoforming operation which shapes the plate in the malleable state in the pocket to a morphology of a region of the limb or joint where the plate is applied, and when the sleeve is worn at the room temperature with the plate in the rigid state in the pocket.

12. The method of claim 11, further comprising:
placing the plate in the pocket;
heating the orthosis to a temperature sufficient to soften the plate; and
placing the sleeve around the limb or joint before the plate hardens.

13. The method of claim 12, wherein the thermoforming operation includes covering the limb or the joint with a film prior to placing the sleeve around the limb or the joint.

14. The method as claimed in claim 12, wherein the thermoforming operation includes placing a pellet on an area of an outer face of the pocket before placing the sleeve around the limb or the joint, the outer face of the pocket being configured to contact skin, and the pellet being removed from the sleeve after the thermoforming operation so as to form a gap between the plate and the skin.

15. The method of claim 11, wherein the formation of the pocket is performed by attaching a layer on an inner face of the sleeve, the layer being configured to contact skin of the limb or the joint to be maintained.

16. A method comprising:
preparing an orthosis comprising a sleeve formed of a single piece of elastic fabric, by
inserting a plate into a pocket formed on the sleeve, the plate being made of a thermoformable material which is in a malleable state at a temperature between 65 and 75° C. and in a rigid state at a room temperature the pocket having a shape corresponding to a shape of the plate, after the orthosis is prepared, performing a thermoforming operation in which the orthosis with the plate in the pocket is heated to a temperature sufficient to set the plate in the malleable state, and before the plate hardens, fitting the orthosis with the plate in the pocket around a region of a limb or a joint of a human or a vertebrate animal, by expanding the sleeve around the region of the limb or joint and then releasing the sleeve such that an elastic tension exerted by the sleeve around the region of the limb or joint pushes the plate in the pocket against the region of the limb or joint such that the plate in the malleable state is shaped to a morphology of the region of the limb or joint where it is applied, wherein a surface of the plate is covered with a coating, the coating being configured to prevent threads of the elastic fabric from being embedded in the plate, the embedding resulting from the thermoforming operation of the plate, the prevention of embedding enabling relative movement of the plate with respect to the elastic fabric forming the pocket when the plate is in the pocket during and after the thermoforming operation, and the sleeve is configured to provide a suitable tension around the limb or the joint, during the thermoforming operation to shape the plate in the pocket to a morphology of the region of the limb or joint where the plate is applied, and when the sleeve is worn at the room temperature with the plate in the rigid state in the pocket.

* * * * *